(12) United States Patent
Arizti et al.

(10) Patent No.: US 11,051,994 B2
(45) Date of Patent: Jul. 6, 2021

(54) ABSORBENT ARTICLE WITH SENSING MEANS

(71) Applicant: The Procter & Gamble Company, Cincinnati, OH (US)

(72) Inventors: Blanca Arizti, Schmitten (DE); Jonathan Livingston Joyce, Independence, KY (US); Steven Jeffrey Specht, Brookfield, CT (US); Grant Edward Anders Striemer, Fairfield Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 560 days.

(21) Appl. No.: 15/445,016

(22) Filed: Feb. 28, 2017

(65) Prior Publication Data
US 2017/0252226 A1 Sep. 7, 2017

(30) Foreign Application Priority Data

Mar. 3, 2016 (EP) .................................... 16158532

(51) Int. Cl.
*A61F 13/15* (2006.01)
*A61F 13/42* (2006.01)
(Continued)

(52) U.S. Cl.
CPC .............. *A61F 13/42* (2013.01); *A61F 13/49* (2013.01); *A61F 13/58* (2013.01); *A61F 13/62* (2013.01);
(Continued)

(58) Field of Classification Search
CPC .......... A61F 13/15; A61F 13/47; A61F 13/53; A61F 13/51; C08L 77/00; A01K 23/00; A47L 13/17
See application file for complete search history.

(56) References Cited

U.S. PATENT DOCUMENTS

| 3,848,594 A | 11/1974 | Buell |
| 3,860,003 A | 1/1975 | Buell |
(Continued)

FOREIGN PATENT DOCUMENTS

| CN | 2562752 Y | 7/2003 |
| CN | 203898554 U | 10/2014 |
(Continued)

OTHER PUBLICATIONS

European Search Report, Application No. 19208865.6, dated Feb. 19, 2020, 6 pages.
(Continued)

*Primary Examiner* — Tatyana Zalukaeva
*Assistant Examiner* — Ilya Y Treyger
(74) *Attorney, Agent, or Firm* — Brian M. Bolam

(57) ABSTRACT

The invention provides an absorbent article comprising an indication means for indicating the presence of bodily exudates, the indication means comprising a color-changing indication means, wherein the absorbent article and the indication means form one integral unit, the article further comprising a indication device, which comprises a housing and a connection means, such that the indication device can be attached to the absorbent article and be detached from the absorbent article, wherein the indication device comprises a color sensor.

2 Claims, 4 Drawing Sheets

(51) Int. Cl.
*A61F 13/58* (2006.01)
*A61F 13/62* (2006.01)
*A61F 13/64* (2006.01)
*G08B 21/20* (2006.01)
*A61F 13/49* (2006.01)
*A61F 13/47* (2006.01)
*A61F 13/53* (2006.01)
*A61F 13/51* (2006.01)
*C08L 77/00* (2006.01)
*A01K 23/00* (2006.01)
*A47L 13/17* (2006.01)

(52) U.S. Cl.
CPC .............. *A61F 13/64* (2013.01); *G08B 21/20* (2013.01); *A61F 2013/422* (2013.01); *A61F 2013/423* (2013.01); *A61F 2013/424* (2013.01); *A61F 2013/426* (2013.01); *A61F 2013/427* (2013.01); *A61F 2013/428* (2013.01); *A61F 2013/429* (2013.01)

(56) References Cited

U.S. PATENT DOCUMENTS

| | | | |
|---|---|---|---|
| 3,911,173 A | 10/1975 | Sprague, Jr. | |
| 4,507,121 A | 3/1985 | Leung | |
| 4,515,595 A | 5/1985 | Kievet et al. | |
| 4,573,986 A | 3/1986 | Minetola et al. | |
| 4,662,875 A | 5/1987 | Hirotsu et al. | |
| 4,681,793 A | 7/1987 | Linman et al. | |
| 4,695,278 A | 9/1987 | Lawson | |
| 4,710,189 A | 12/1987 | Lash | |
| 4,785,996 A | 11/1988 | Ziecker et al. | |
| 4,795,454 A | 1/1989 | Dragoo | |
| 4,808,178 A | 2/1989 | Aziz | |
| 4,842,666 A | 6/1989 | Werenicz | |
| 4,846,815 A | 7/1989 | Molloy | |
| 4,894,060 A | 1/1990 | Nestegard | |
| 4,909,803 A | 3/1990 | Aziz et al. | |
| 4,946,527 A | 8/1990 | Battrell | |
| 4,963,140 A | 10/1990 | Robertson et al. | |
| 5,036,859 A | 8/1991 | Brown | |
| 5,137,537 A | 8/1992 | Herron et al. | |
| 5,151,092 A | 9/1992 | Buell et al. | |
| 5,221,274 A | 6/1993 | Buell et al. | |
| 5,242,436 A | 9/1993 | Weil et al. | |
| 5,499,978 A | 3/1996 | Buell et al. | |
| 5,507,736 A | 4/1996 | Clear et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,591,152 A | 1/1997 | Buell et al. | |
| 5,700,254 A | 12/1997 | McDowall et al. | |
| 5,865,823 A | 2/1999 | Curro | |
| 5,938,648 A | 8/1999 | Lavon et al. | |
| 6,004,306 A | 12/1999 | Robles et al. | |
| 6,432,098 B1 | 8/2002 | Kline et al. | |
| 6,632,504 B1 | 10/2003 | Gillespie et al. | |
| 6,645,569 B2 | 11/2003 | Cramer et al. | |
| 6,863,933 B2 | 3/2005 | Cramer et al. | |
| 6,946,585 B2 | 9/2005 | Brown | |
| 7,112,621 B2 | 9/2006 | Rohrbaugh et al. | |
| 7,786,341 B2 | 8/2010 | Schneider et al. | |
| 8,111,165 B2 | 2/2012 | Ortega et al. | |
| 9,380,977 B2 * | 7/2016 | Abir | A61F 13/42 |
| 2003/0105190 A1 | 6/2003 | Diehl et al. | |
| 2003/0148684 A1 | 8/2003 | Cramer et al. | |
| 2005/0008839 A1 | 1/2005 | Cramer et al. | |
| 2005/0195085 A1* | 9/2005 | Cretu-Petra | A61B 5/6808 340/573.5 |
| 2006/0224135 A1* | 10/2006 | LaVon | A61F 13/15203 604/385.14 |
| 2008/0086103 A1* | 4/2008 | McKiernan | G01K 13/002 604/385.02 |
| 2008/0147030 A1 | 6/2008 | Nhan et al. | |
| 2008/0312622 A1 | 12/2008 | Hundorf et al. | |
| 2009/0057025 A1 | 6/2009 | Song et al. | |
| 2009/0275908 A1* | 11/2009 | Song | A61F 13/42 604/361 |
| 2009/0326417 A1 | 12/2009 | Ales, III et al. | |
| 2010/0164733 A1 | 7/2010 | Ales et al. | |
| 2012/0215190 A1 | 8/2012 | Kawashima | |
| 2014/0155850 A1 | 6/2014 | Kawashima | |

FOREIGN PATENT DOCUMENTS

| | | |
|---|---|---|
| EP | 149880 | 7/1985 |
| EP | 2679209 | 1/2014 |
| EP | 2740450 | 6/2014 |
| EP | 2 832 323 A1 * | 2/2015 |
| WO | WO 95/10996 | 4/1995 |
| WO | WO 95/11652 | 5/1995 |
| WO | WO 95/16746 | 6/1995 |
| WO | WO 99/34841 | 7/1999 |
| WO | WO 99/34842 | 7/1999 |
| WO | WO 2000/59430 | 10/2000 |
| WO | WO 02/064877 | 8/2002 |
| WO | WO 02/067809 | 9/2002 |
| WO | WO 2007/122524 | 11/2007 |
| WO | WO 2008/155699 | 12/2008 |
| WO | WO 2012/052172 | 4/2012 |

OTHER PUBLICATIONS

Extended European Search Report and Search Opinion; Application No. 16156532.8; dated Sep. 7, 2016; 7 pages.
Extended European Search Report and Search Opinion; Application No. 17158380.0; dated May 4, 2017; 7 pages.
International Search Report and Written Opinion; Application Ser. No. PCT/US2017/019799; dated May 4, 2017, 11 pages.

* cited by examiner

ABSORBENT ARTICLE WITH SENSING MEANS

FIELD OF THE INVENTION

The invention provides an absorbent article for personal hygiene such as a baby diaper, a training pant or an adult incontinence product.

BACKGROUND OF THE INVENTION

Absorbent articles for personal hygiene, such as disposable diapers for infants, training pants for toddlers or adult incontinence undergarments are designed to absorb and contain bodily exudates, in particular large quantity of urine. A relevant absorbent article can also be provided in the form of an incontinence insert to be inserted into an undergarment or in form of a pad, including feminine care pads. These absorbent articles comprise several layers providing different functions, for example a topsheet, a backsheet and in-between an absorbent core, among other layers.

The function of the absorbent core is to absorb and retain the exudates for a prolonged amount of time, for example overnight for a diaper, minimize re-wet to keep the wearer dry and avoid soiling of clothes or bed sheets. The majority of currently marketed absorbent articles comprise as absorbent material a blend of comminuted wood pulp with superabsorbent polymers (SAP) in particulate form, also called absorbent gelling materials (AGM), see for example U.S. Pat. No. 5,151,092 (Buell). Absorbent articles having a core consisting essentially of SAP as absorbent material (so called "airfelt-free" cores) have also been proposed but are less common than traditional mixed cores (see e.g. WO2008/155699 (Hundorf), WO95/11652 (Tanzer), WO2012/052172 (Van Malderen)).

U.S. Pat. No. 8,111,165 B2 discloses a sensor to sense a condition such as pressure from body weight or moisture from incontinence. The sensor comprises a signal processing unit, a transmitter and a power supply, typically in form of a battery. These elements are arranged on a flexible substrate in low profile enabling disposition adjacent to the human body. Moreover, a transmitter antenna is to be provided on the substrate.

While this device allows monitoring conditions of the human body and can also be used as a moisture sensor, it represents also relatively costly solution. It would not be seen appropriate to dispose of the sensor together with a (disposable) absorbent article. If the sensor, however, is to be reduced, the sensing area has potentially been exposed to moisture. Therefore this concept does not allow for simple usage.

The present invention attempts to overcome the disadvantages of the prior art. The present invention provides an absorbent article with an improved sensing means. While the sensing means provides useful and reliable information about the state of the absorbent article, in particular whether it has received bodily exudates, the present invention still allows for an inexpensive solution. It is therefore also an objective of the present invention to allow for sensing means, which can be reused in part and which can be disposed of in part. It has also been found, that it is desirable to provide an absorbent article with sensing means, which can be efficiently produced on commercially available equipment at high process speeds.

SUMMARY OF THE INVENTION

The invention provides an absorbent article for personal hygiene such as a baby diaper, a training pant or an adult incontinence product. More particularly, the invention concerns an absorbent article for personal hygiene, designed to absorb and contain bodily exudates such as a diaper (10), or training pant, or incontinence insert, the absorbent article having a front edge (12) and a rear edge (14), a longitudinal axis extending in a longitudinal direction of the article, the article having a length L as measured along the longitudinal axis from the front edge to the back edge, the absorbent article comprising: an indication means (60) for indicating the presence of such bodily exudates, the indication means (60) comprising a color-changing indication means (60), wherein the absorbent article and the indication means (60) form one integral unit, the article further comprising a indication device (70), which comprises a housing and a connection means (68), such that the indication device (70) can be attached to the absorbent article and be detached from the absorbent article, wherein the indication device (70) comprises a color sensor.

DETAILED DESCRIPTION OF THE INVENTION

Introduction

Figure 1:
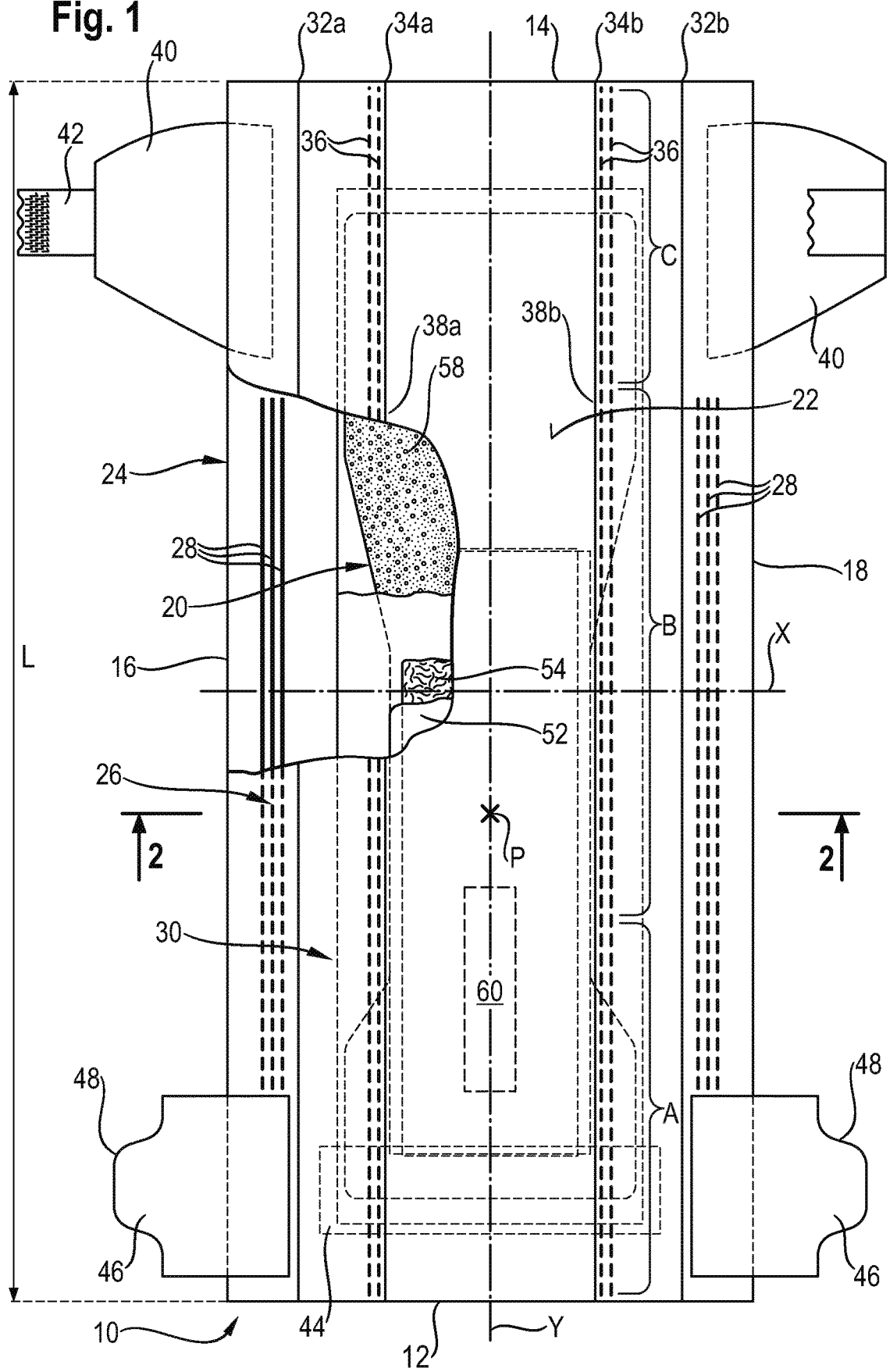
FIG. 1 is a top view of an absorbent article according to an embodiment of the present invention in the form of a diaper with some layers partially removed.

As used herein, the term "absorbent article" refers to disposable devices such as infant or adult diapers, training pants, and the like which are placed against or in proximity to the body of the wearer to absorb and contain the various exudates discharged from the body. Typically these articles comprise a topsheet, backsheet, an absorbent core and optionally an acquisition system (which may be comprised of one or several layers) and typically other components, with the absorbent core normally placed between the backsheet and the acquisition system or topsheet.

The absorbent articles of the invention will be further illustrated in the below description and in the Figures in the form of a taped diaper. Nothing in this description should be however considered limiting the scope of the claims unless explicitly indicated otherwise. Unless indicated otherwise, the description refers to the dry article, i.e. before use and conditioned at least 24 hours at 21° C.+/−2° C. and 50+/−20% Relative Humidity (RH).

A "nonwoven web" as used herein means a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding and airlaying. The basis weight of nonwoven webs is usually expressed in grams per square meter ($g/m^2$ or gsm).

The term "joined" or "bonded" or "attached", as used herein, encompasses configurations whereby an element is directly secured to another element by affixing the element directly to the other element, and configurations whereby an element is indirectly secured to another element by affixing the element to intermediate member(s) which in turn are affixed to the other element.

"Comprise," "comprising," and "comprises" are open ended terms, each specifies the presence of what follows, e.g., a component, but does not preclude the presence of other features, e.g., elements, steps, components known in the art, or disclosed herein. These terms based on the verb "comprise" should be read as encompassing the narrower terms "consisting of" which excludes any element, step, or ingredient not specified and "consisting essentially of" which limits the scope of an element to the specified materials or steps and those that do not materially affect the way the element performs its function. Any preferred or exemplary embodiments described below are not limiting the scope of the claims, unless specifically indicated to do so. The words "typically", "normally", "advantageously" and the likes also qualify elements which are not intended to limit the scope of the claims unless specifically indicated to do so.

General Description of the Absorbent Article

According to the present invention the article comprises an indication means for indicating the presence of bodily exudates. This indication means, according to the present invention, comprises a color-changing indication means. The indication means might also comprise additional indication means, for example, a resistance sensitive indication means. Resistance sensitive indication means can be provided for example by providing two electrically conductive units at a given spatial distance. If bodily exudates, which typically comprise liquid portion, come in contact with the two electrically conductive means, the resistance between the two electrically conductive means is reduced. Other indication means, as known in the field in the context for sensor for absorbent articles, can also be useful. In any case, however, the color sensitive indication means provides an additional and often the central indication means in the context of the present invention.

The absorbent article and the indication means are provided to form one integral unit. For forming one integral unit, the indication means can be directly or indirectly attached to the article. Direct or indirect attachment to the article is typically to one distinguishable element of the article. For example, it can be useful to attach the indication means to the back sheet of the article, such that the indication means and the back sheet of the article from one integral unit. For example if the indication means is provided in sheet form, the respective sheet can be adhesively attached to the back sheet of the article. The respective sheet could also be provided from one and the same material with the back sheet, this material however being treated in suitable ways as to provide an indication means in a pre-defined area.

According to the present invention further an indication device is provided. The indication device comprises a housing and a connection means. The connection means is provided such that the indication device can be attached to the absorbent article and can be detached from the absorbent article. It is normally useful, that the indication device can be attached to the integral unit and can be detached from the integral unit. It is normally useful, that the indication device can be attached to an area of the absorbent article, which comprises the integral unit and can be detached from that area of the absorbent article.

The housing of the indication device will have an outer extension in a first direction and an outer extension in a second direction, which is perpendicular to the first direction. The first direction is to be chosen as a characteristic directions, e.g. along a main axis and normally as that of largest extension of the housing. For safety and convenient handling of the device, it is useful that the device has a length in the first direction of at least 1 cm, 2 cm, 3 cm, 4 cm or more (but normally less than 15 cm) and that the device has a length in the second direction of at least 1 cm, 2 cm, 3 cm or more (but normally less than 15 cm). The housing can be rigid or at least partially or fully flexible. To be flexible in can incorporate flexible electronic components (and boards).

According to the present invention, the indication device comprises a color sensor. This color sensor can generate an output which depends on a color observed by the color sensor. It can also be referred to as an optical sensor. A useful color sensor can comprise a photo-diode. The example color sensor TCS 34725 has been found useful.

Often, the indication device will also comprise a light emitting device, such as an LED, for emitting light onto an area, the color of which is to be assessed by the color sensor. The color sensor is in particular optimized for assessing the color of the color-changing indication means. The color sensor might be sensitive to visible and non-visible light, namely light in the near IR range. Sensor of this type are referred to as hyperspectral sensors. The color sensitive indication means can change its color, and will namely change its color based on the presence of bodily exudates. The color sensor will therefore provide an output, which varies depending on the presence of bodily exudates.

In the context of the present invention essentially any known color-changing indication means can be useful. It is often useful to employ a color-changing indication means which comprises a chemical substance. Such a chemical substance can induce a color change when bodily exudates are present.

One useful form of a color-changing indication means comprises a pH-sensitive sensor. Bodily exudates will typically influence the pH-value in their environment. A pH-sensitive sensor, which changes color is therefore useful.

Other useful indication means can comprise biological or physical sensor materials. The skilled person is aware of numerous useful biological sensor materials. Physical sensors can be provided by a material, which changes its color when the material is stretched. Stretching of a material can be induced by the swelling of the absorbent core.

Additionally the indication means can comprise a material selected from the group consisting of thermochromic inks, thermochromic dyes, thermochromic liquid crystalline materials, and combinations thereof. These indication means can, for example, serve for additional body temperature or fever indication.

The present invention can usefully employ connection means which allow for detachment and can also allow for refastening of an indication device to the absorbent article. Such means comprise adhesive means. Such means further comprise mechanical fastening means, including strap based fastening mean or means comprising at least one button or at least one magnet. Among the group of mechanical fastening means, a hook-end-loop fastener is useful. It can be useful to attach the hook-portion to the absorbent article or to attach the loop-portion to the absorbent article. The corresponding portion can then be attached to the indication device.

In one useful embodiment of the present invention, the loop portion of a hook-and-loop-fastener can be provided integral with the absorbent article. For example, if the outer side of the backsheet of the absorbent article is provided from a textile material, e.g. a non-woven material, loops provided in such a material can interact with the hooks of a hook-portion of a fastener.

There is also alternative forms of mechanical fastening means (to be used as connection means), which can be used additionally or alternatively. For example, a pocket can be formed in an area of the absorbent article. For example, such a pocket can be formed between layers of the backsheet. A pocket can also be formed between other layers. For example, diapers can be provided as pant-diapers comprising a crotch-portion and a belt-portion. The crotch-portion and the belt-portion can be joined adhesively or mechanically, e.g. by crimping. In the area of adhesive joining, a certain portion can be free of adhesive and accessible from the outside. This portion can than serve as a pocket for receiving the indication device.

A useful indication device will provide information which in one aspect will indicate the presence of bodily exudates. Such indication device can comprise a variety of output or display elements. A simple output element can comprise LED or similar lamps. For example a green light can be used as an indication for the absence of bodily exudates or presence only a low amount of bodily exudates whereas a red light can indicate the presence of a higher amount of bodily exudates and therefore will normally indicate the need to change the absorbent article. Information can be provided in more comprehensive forms and therefore a display element, for example in the form of a small monitor can be useful. Information to be displayed on such a monitor or similar display element could include information about the loading status of the absorbent article, the time at which a fresh absorbent article has been applied and so forth.

The output element or display element can be provided within the housing or attached to the indication device. The output or display element can also be provided in a separate unit. Such a separate unit can also have other functions. It can be useful to employ a mobile phone with a display or another personal digital assistant for use as a display element in the present context. The display element can also be a computer (including a laptop computer or a tablet computer). Information obtained from the indication device can also be displayed on several such unit at the same time. This can be displayed there in the same format or in similar formats. For example a more detailed display of information on a computer can be combined with simplified display of information on a mobile phone. Additionally or alternatively the output element can also comprise acoustic indication device and can also rely on a computer generated voice. In some cases also, the information is not or not only displayed or provided, but directed to a data storage device for data aggregation.

For providing information to the separate unit the indication device can be provided with broadcasting means for sending information to the unit comprising the display element. The skilled person is aware of useful standards for providing such broadcasting means, for example the Bluetooth standard can be employed, or Wifi broadcasting can be used, or radio frequency can be used (as in RFID technology). Additionally or alternatively an acoustic broadcasting is useful.

In a further aspect, the present invention relates to a kit comprising a multitude of absorbent articles and an indication device, which comprises a housing and a connection means, such that the indication device can be connected to any one of the absorbent articles. The absorbent articles and the indication device may each comprise any of the further features described herein. Hence, the indication device can be used on a first absorbent article of the multitude, the absorbent article can be disposed of after use, and the indication device can be re-used on another (fresh) absorbent article.

Figure 2:
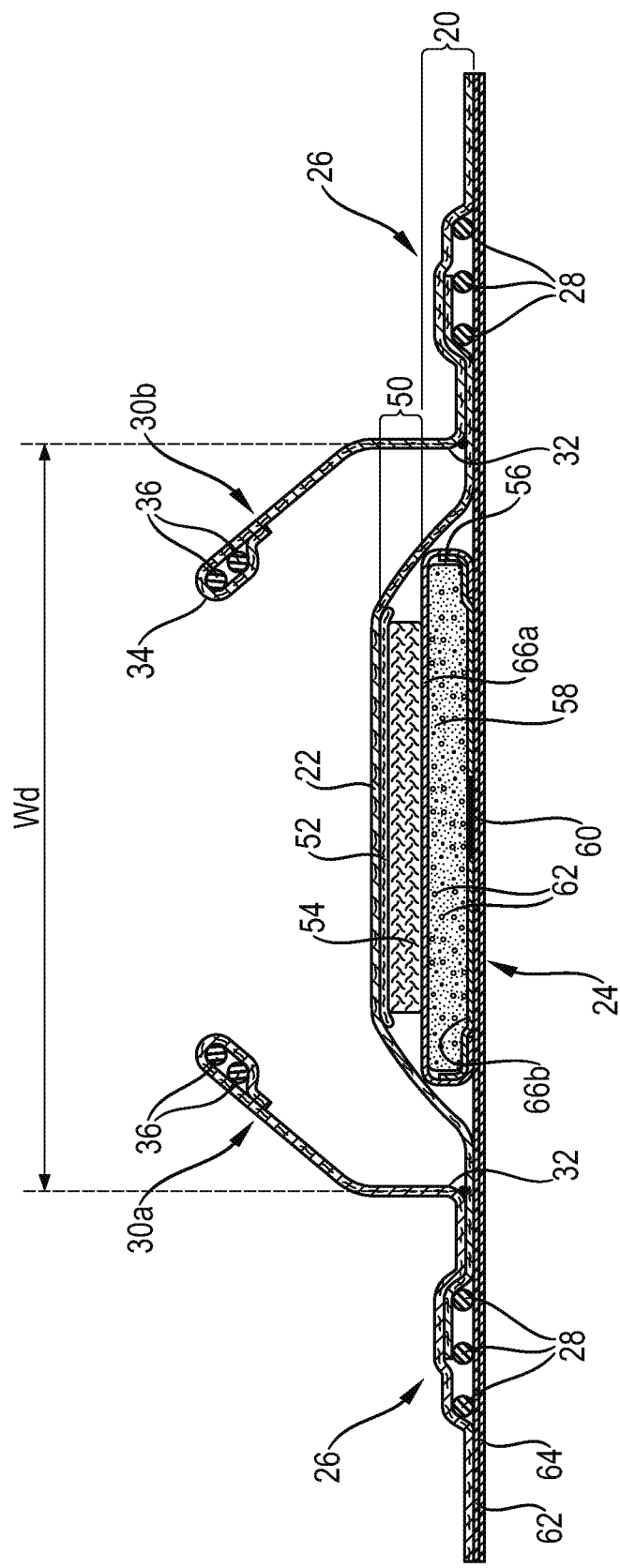
FIG. 2 is a transversal cross-section of the embodiment of FIG. 1 at the crotch area.

An exemplary absorbent article according to the invention in the form of an infant diaper 10 is represented in FIGS. 1 and 2.

FIG. 1 is a plan view of the exemplary diaper 10, in a flattened state, with portions of the structure being cut-away to more clearly show the construction of the diaper 10. This diaper 10 is shown for illustration purpose only as the invention may be used for making a wide variety of diapers or other absorbent articles. The diaper extends from a front edge 12 to a longitudinally opposed rear edge 14. It comprises left side edge 16 and transversally opposed right side edge 18. The diaper 10 comprises an absorbent core which is positioned between topsheet 22, which is at least partially liquid permeable and backsheet 24, which is essentially impermeable to liquid.

In FIG. 1 "X" denotes a transversal access through the geometrical center of the diaper, and axis "Y" denotes the longitudinal direction. The area A denotes the front area of the diaper as seen in the longitudinal direction and C denotes the rear area of the diaper as seen in the longitudinal direction, and B denotes the central area or crotch area positioned between area A and area B, in the longitudinal direction. L denotes the length of the diaper from the front edge 12 to rear edge 14 as measured in the longitudinal direction.

The article comprises a crotch point P defined herein as the point placed on the longitudinal axis at a distance of two fifth (⅖) of L starting from the front edge 12 of the diaper 10.

The absorbent article comprises an indication means 60, which can take the form of a small sheet of material or patch. As shown, a rectangular form is useful. The indication means 60 can be arranged in the front area A, the central area B or the rear area C of the diaper. It is often useful to range the indication means 60 in the central area B or in the front area A. As shown, it can be useful to provide the indication means 60 towards the front of the crotch point P.

The diaper 10 further comprises gasketing cuffs 26 for maintaining a tight fit of the diaper 10 to the wearer, when the diaper 10 is worn. The gasketing cuffs 26 comprise elastics 28 for maintaining the tight fit, which helps to avoid leakage.

The diaper 10 further comprises barrier leg cuffs 30 on each side of the diaper. Barrier leg cuffs comprise proximal edges 32a and 32b, which are adjacent to topsheet 22. Opposed to the respective proximal edges, the barrier leg cuffs 30 comprise distal edges 34a and 34b, respectively. In the area of the distal edges 34, further elastics 36a provided, while a portion of the distal edges 34 of the barrier leg cuffs 30 can be attached to components of the diaper 10, such as the topsheet 22, it is preferred that the barrier leg cuffs 30 also comprise unattached areas of the distal edges, herein referred to as free flaps 38. The respective free flaps 38 are typically provided in the central zone of the diaper 10.

The diaper 10 further comprises the fastening system, for fastening the diaper to the body of a wearer. This fastening system comprises two back ears 40, which comprise adhesive tapes 42. The adhesive tapes 42 can be attached to landing zone 44. In the front area, the diaper comprises front ears 46. As described below, for other embodiments other fastening systems can be useful, including mechanical fasteners and including fastening systems comprising more than two, for example for IS.

The core can optionally comprise areas, where there is a reduced amount of absorbent material or no absorbent material. These areas are referred to as channels.

FIG. 2 is transversal cross-section of the embodiment of FIG. 1 and readily shows other structural elements of the diaper. As shown in this figure, the diaper comprises an acquisition-distribution system 50. This acquisition-distribution system comprises acquisition layer 52, which first receives liquid, and distribution layer 54 underneath acquisition layer 52.

The absorbent core 20 comprises a core layer 56. This core layer can comprise particular material, such as super absorbent particles, herein also referred to SAP. Between the core layer 56 and the backsheet 24 the indication means 60 can be arranged. As shown in FIG. 2 the backsheet 24 can comprise and inner backsheet layer 62 (which is oriented towards the core 20) and an outer backsheet layer 64, which is generally oriented towards the garments of a wearer. As shown in FIG. 2, in accordance with the present invention the indication means 60 can be provided above the inner backsheet layer and below the core wrap, more precisely, below the portion of the core wrap 66 which is oriented towards the backsheet 24.

Figure 3:
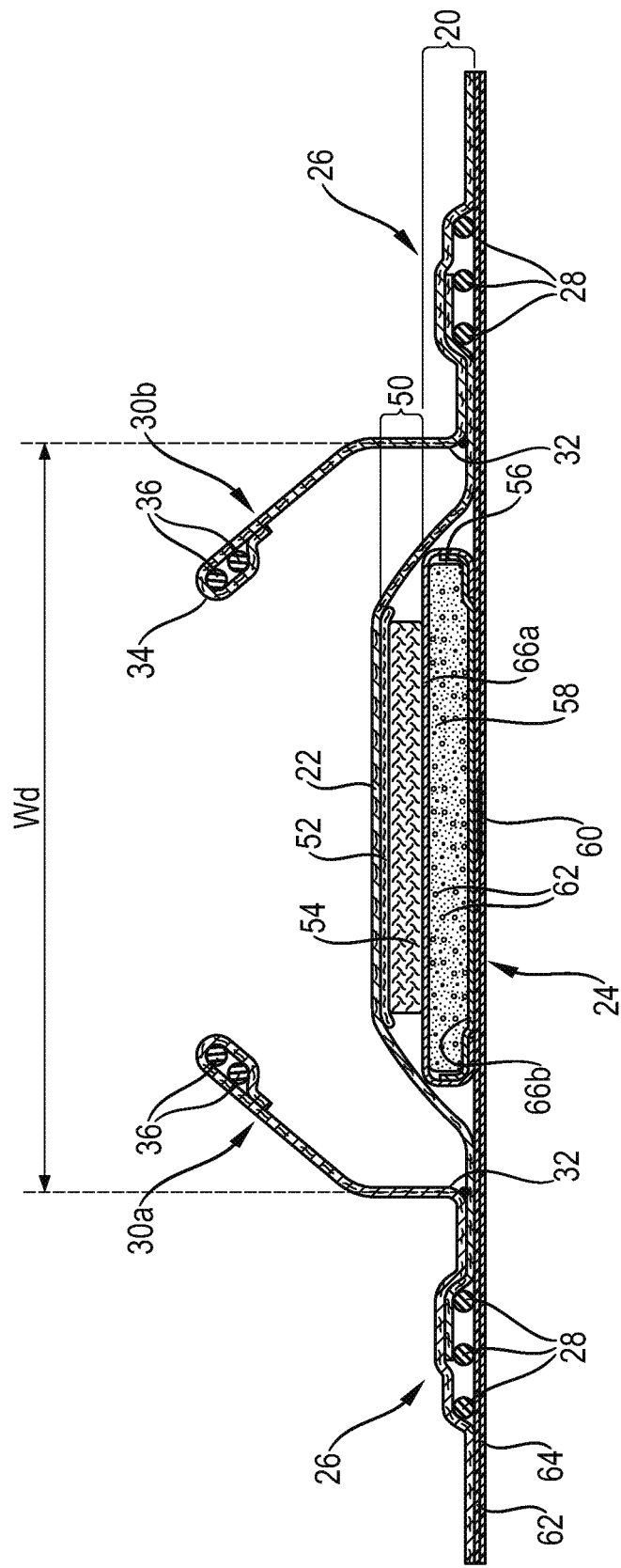
FIG. 3 is a corresponding transversal cross-section of another embodiment of an absorbent article.

FIG. 3 shows an alternative embodiment of the present invention. This embodiment resembles that shown in FIGS. 1 and 2. However, the indication means 60 is arranged here between the inner backsheet layer 62 and the outer backsheet layer 64.

Figure 4:
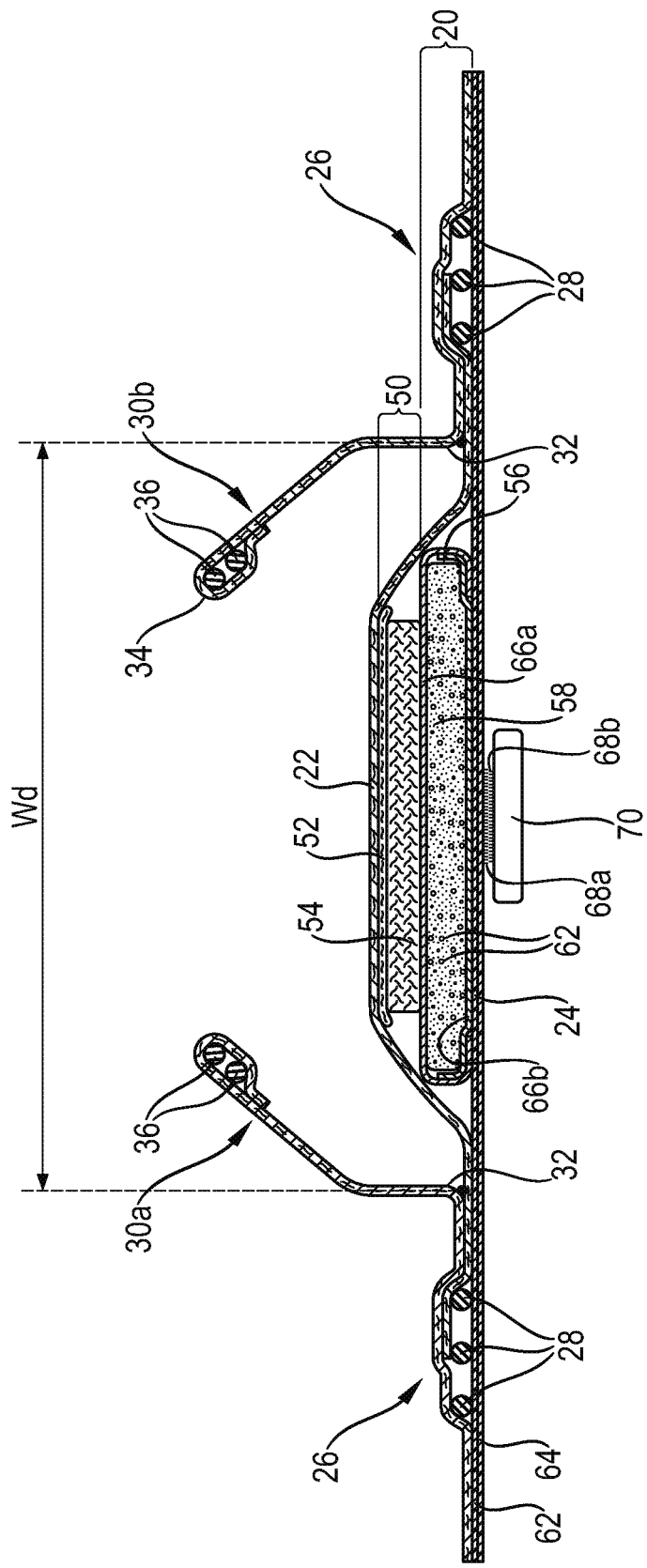
FIG. 4 is a further corresponding transversal cross-section of an embodiment of the present invention.

FIG. 4 shows another aspect of the present invention. For the embodiment shown in FIG. 2 the absorbent article is shown together with indication device 70. As shown, indication device 70 can take the form of a small pod which can have generally rectangular cross sections. The indication device 70 can be attached to the backsheet 24 of the diaper 10 by mechanical fastening means 68. The mechanical fastening means can comprise a first component and a second component. The first component can be attached to backsheet 24 and the second component can be attached to indication device 70. The two components interact with each other, for example hook and loop fasteners can be used. The respective component can be adhesively joined to the backsheet and to the indication device 70, respectively.

The article may also comprise elasticized gasketing cuffs 26 joined to the chassis of the absorbent article, typically via the topsheet and/or backsheet, and substantially planar with the chassis of the diaper.

The Figures also show typical taped diaper components such as a fastening system comprising adhesive tabs 42 attached towards the back edge of the article and cooperating with a landing zone 44 on the front of the article. The absorbent article may also comprise other typical elements, which are not represented, such as a back elastic waist feature, a front elastic waist feature, transverse barrier cuff(s), a lotion application, etc. . . .

The topsheet 22, the backsheet 24, the absorbent core 20 and the other article components may be assembled in a variety of well known configurations, in particular by gluing or heat embossing. Exemplary diaper configurations are described generally in U.S. Pat. Nos. 3,860,003, 5,221,274, 5,554,145, 5,569,234, 5,580,411, and 6,004,306. The absorbent article is preferably thin. The caliper at the crotch point P of the article may be for example from 4.0 mm to 12.0 mm, in particular from 6.0 mm to 10.0 mm, as measured with a suitable caliper test, for example the Absorbent Article Caliper Test disclosed in EP 2 740 450 A1 (Applicant: The Procter & Gamble Company).

These and other components of the articles will now be discussed in more details.

Topsheet 22

The topsheet 22 is the part of the absorbent article that is directly in contact with the wearer's skin. The topsheet 22 can be joined to the backsheet 24, the core 20 and/or any other layers as is known in the art. Usually, the topsheet 22 and the backsheet 24 are joined directly to each other in some locations (e.g. on or close to the periphery of the article) and are indirectly joined together in other locations by directly joining them to one or more other elements of the diaper 10.

The topsheet 22 is preferably compliant, soft-feeling, and non-irritating to the wearer's skin. Further, at least a portion of the topsheet 22 is liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or combinations thereof, e.g. a combination of natural and synthetic fibers. A combination of materials can be achieved by combining at least two materials by means of needle punching, ultra-sonic bonding, ring rolling, embossing, gluing or other types of mechanical entanglement. The resulting material may maintain a dual/multiple layer structure, but may also loose a structure of distinguishable layers after such process steps. It can also be useful to provide a formed film patch underneath the topsheet.

If the topsheet 22 includes fibers, the fibers may be spunbond, carded, wet-laid, meltblown, hydroentangled, or otherwise processed as is known in the art, in particular spunbond PP nonwoven. A suitable topsheet comprising a web of staple-length polypropylene fibers is manufactured by Veratec, Inc., a Division of International Paper Company, of Walpole, Mass. under the designation P-8.

The topsheet 22 may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" from the article is increased. Typically, the total area of the apertures at the surface of a diaper may have an area of between about 10 mm$^2$ and about 50 mm$^2$, in particular between about 15 mm$^2$ and 35 mm$^2$. Examples of apertured topsheet are disclosed in U.S. Pat. No. 6,632,504, assigned to BBA NONWOVENS SIMPSONVILLE. WO2011/163582 also discloses suitable colored topsheet having a basis weight of from 12 to 18 gsm and comprising a plurality of bonded points. Each of the bonded points has a surface area of from 2 mm$^2$ to 5 mm² and the cumulated surface area of the plurality of bonded points is from 10 to 25% of the total surface area of the topsheet.

Typical diaper topsheets have a basis weight of from about 10 to about 21 gsm, in particular between from about 12 to about 18 gsm but other basis weights are possible.

Backsheet 24

The backsheet 24 is generally that portion of the diaper 10 positioned adjacent the garment-facing surface of the absorbent core 20 and which prevents the exudates absorbed and contained therein from soiling articles such as bedsheets and undergarments. The backsheet 24 is typically impermeable to liquids (e.g. urine). The backsheet may for example be or comprise a thin plastic film such as a thermoplastic film having a thickness of about 0.012 mm to about 0.051 mm. Exemplary backsheet films include those manufactured by Tredegar Corporation, based in Richmond, Va., and sold under the trade name CPC2 film. Other suitable backsheet materials may include breathable materials which permit vapors to escape from the diaper 10 while still preventing exudates from passing through the backsheet 24. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va., and sold under the designation EXAIRE, and monolithic films such as manufactured by Clopay Corporation, Cincinnati, Ohio under the name HYTREL blend P18-3097. Some breathable composite materials are described in greater detail in PCT Application No. WO 95/16746 published on Jun. 22, 1995 in the name of E. I. DuPont; U.S. Pat. No. 5,938,648 to LaVon et al., U.S. Pat. No. 4,681,793 to Linman et al., U.S. Pat. No. 5,865,823 to Curro; and U.S. Pat. No. 5,571,096 to Dobrin et al, U.S. Pat. No. 6,946,585B2 to London Brown.

The backsheet 24 may be joined to the topsheet 22, the absorbent core 20 or any other element of the diaper 10 by any attachment means known in the art. Suitable attachment means are described above with respect to means for joining the topsheet 22 to other elements of the diaper 10. For example, the attachment means may include a uniform continuous layer of adhesive, a patterned layer of adhesive, or an array of separate lines, spirals, or spots of adhesive. Suitable attachment means comprises an open pattern network of filaments of adhesive as disclosed in U.S. Pat. No. 4,573,986. Other suitable attachment means include several lines of adhesive filaments which are swirled into a spiral pattern, as is illustrated by the apparatus and methods shown in U.S. Pat. Nos. 3,911,173, 4,785,996; and 4,842,666. Adhesives which have been found to be satisfactory are manufactured by H. B. Fuller Company of St. Paul, Minn. and marketed as HL-1620 and HL 1358-XZP. Alternatively, the attachment means may comprise heat bonds, pressure bonds, ultrasonic bonds, dynamic mechanical bonds, or any other suitable attachment means or combinations of these attachment means as are known in the art.

Absorbent Core 20

As used herein, the term "absorbent core" refers to the component or components of the article having the most absorbent capacity and comprising an absorbent material and optionally a core wrap enclosing the absorbent material. The term "absorbent core" does not include the acquisition-distribution system or layer or any other component of the article which is not either integral part of the core wrap or placed within the core wrap. The core may consist essentially of, or consist of, a core wrap, absorbent material as defined below and glue enclosed within the core wrap.

The absorbent core 20 of the invention comprises a first core layer 56 and a second core layer 58. As explained, the absorbent article might comprise and acquisition distribution system, which will typically consist of one or more layers. Most typically, the layers are arranged above the core layer. Hence, a number of layers can be arranged between the topsheet and the backsheet. The skilled person will usually have no difficulty in distinguishing between these layers. In case of doubt, a core layer can be identified as being a layer which is generally less permeable than a layer forming part of the acquisition-/distribution-system.

Permeability generally refers to the quality of a porous material that causes it to a lower liquid or gases to pass through it. Hence, the layers of the acquisition distribution system should generally be more permeable than the layers of the core system. As these layers are meant to distribute liquid to the absorbent core, where the liquid is ultimately stored.

The absorbent core can comprise absorbent material with a varying amount of superabsorbent polymers (herein abbreviated as "SAP"), often enclosed within a core wrap. The SAP content can represent from 0% to 80% by weight of the absorbent material contained in the core wrap. Often an SAP content of 20% to 50% by weight of the absorbent material contained in the core wrap is useful. The core wrap is not considered as absorbent material for the purpose of assessing the percentage of SAP in the absorbent core.

By "absorbent material" it is meant a material which has some absorbency property or liquid retaining properties, such as SAP, cellulosic fibers as well as synthetic fibers. Herein, absorbent materials in the form of fibrous absorbent materials have been found to be useful. These fibrous absorbent materials can comprise or consist of natural fibers, e.g. cellulosic fibers as well as synthetic fibers. Typically, glues used in making absorbent cores have no absorbency properties and are not considered as absorbent material.

The SAP content may be higher than 30%, for example at least 40%, at least 50%, at least 80% of the weight of the absorbent material contained within the core wrap. The absorbent material may in particular comprises from 10 to 70, for example 30 to 60 weight percent of natural or synthetic fibers.

The absorbent core may comprise a generally planar top edge and a generally planar bottom edge. In some embodiments, the absorbent material will be advantageously distributed in higher amount towards the front edge than towards the rear edge as more absorbency is required at the front. In other embodiments, typically embodiments for other uses of an absorbent article, such as care of elderly incontinent people versus care of babies, the absorbent material will be advantageously distributed in higher amount towards the rear edge than towards the front edge as more absorbency is required at the rear area.

The core wrap may be formed by two separate sheets of nonwoven material which may be at least partially sealed along the edges of the absorbent core. The core wrap may be at least partially sealed along its front edge, back edge and two longitudinal edges so that substantially no absorbent material leaks out of the absorbent core wrap.

The absorbent core of the invention may further comprise adhesive for example to help immobilizing the SAP within the core wrap and/or to ensure integrity of the core wrap, in particular when the core wrap is made of two or more substrates. Such an adhesive can be provided in the form of fibrous thermoplastic adhesive material.

The fibrous thermoplastic adhesive material may be at least partially in contact with the superabsorbent material in the land areas and at least partially in contact with the substrate layer in the junction areas. This imparts an essentially three-dimensional structure to the fibrous layer of thermoplastic adhesive material, which in itself is essentially a two-dimensional structure of relatively small thickness, as compared to the dimension in length and width directions. Thereby, the fibrous thermoplastic adhesive material may provide cavities to cover the absorbent material in the land area, and thereby immobilizes this absorbent material.

The thermoplastic adhesive material may comprise, in its entirety, a single thermoplastic polymer or a blend of thermoplastic polymers, having a softening point, as determined by the ASTM Method D-36-95 "Ring and Ball", in the range between 50° C. and 300° C., and/or the thermoplastic adhesive material may be a hotmelt adhesive comprising at least one thermoplastic polymer in combination with other thermoplastic diluents such as tackifying resins, plasticizers and additives such as antioxidants.

Superabsorbent Polymer (SAP)

Superabsorbent material, herein also referred to as superabsorbent polymer material, superabsorbent polymers or SAP, refers to absorbent materials which are cross-linked polymeric materials that can absorb at least 10 times their weight of an aqueous 0.9% saline solution as measured using the Centrifuge Retention Capacity (CRC) test (EDANA method WSP 241.2-05E). The SAP used may in particular have a CRC value of more than 20 g/g, or more than 24 g/g, or of from 20 to 50 g/g, or from 20 to 40 g/g, or 24 to 30 g/g. The SAP useful in the present invention include a variety of water-insoluble, but water-swellable polymers capable of absorbing large quantities of fluids.

The superabsorbent polymer can be in particulate form so as to be flowable in the dry state. Typical particulate absorbent polymer materials are made of poly(meth)acrylic acid polymers. However, e.g. starch-based particulate absorbent polymer material may also be used, as well polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. The superabsorbent polymer may be polyacrylates and polyacrylic acid polymers that are internally and/or surface cross-linked.

The SAP useful for the present invention may be of numerous shapes. The term "particles" refers to granules, fibers, flakes, spheres, powders, platelets and other shapes and forms known to persons skilled in the art of superabsorbent polymer particles. In some embodiments, the SAP particles can be in the shape of fibers, i.e. elongated, acicular superabsorbent polymer particles. In those embodiments, the superabsorbent polymer particles fibers have a minor dimension (i.e. diameter of the fiber) of less than about 1 mm, usually less than about 500 μm, and preferably less than 250 μm down to 50 μm. The length of the fibers is preferably about 3 mm to about 100 mm. The fibers can also be in the form of a long filament that can be woven.

Typically, SAP are spherical-like particles. In contrast to fibers, "spherical-like particles" have a longest and a smallest dimension with a particulate ratio of longest to smallest particle dimension in the range of 1-5, where a value of 1 would equate a perfectly spherical particle and 5 would allow for some deviation from such a spherical particle. The superabsorbent polymer particles may have a particle size of less than 850 or from 50 to 850 preferably from 100 to 710 more preferably from 150 to 650 as measured according to EDANA method WSP 220.2-05. SAP having a relatively low particle size help to increase the surface area of the absorbent material which is in contact with liquid exudates and therefore support fast absorption of liquid exudates.

The SAP may have a particle sizes in the range from 45 μm to 4000 μm, more specifically a particle size distribution within the range of from 45 μm to about 2000 μm, or from about 100 μm to about 1000, 850 or 600 μm. The particle size distribution of a material in particulate form can be determined as it is known in the art, for example by means of dry sieve analysis (EDANA 420.02 "Particle Size distribution).

In some embodiments herein, the superabsorbent material is in the form of particles with a mass medium particle size up to 2 mm, or between 50 microns and 2 mm or to 1 mm, or preferably from 100 or 200 or 300 or 400 or 500 μm, or to 1000 or to 800 or to 700 μm; as can for example be measured by the method set out in for example EP-A-0,691, 133. In some embodiments of the invention, the superabsorbent polymer material is in the form of particles whereof at least 80% by weight are particles of a size between 50 μm and 1200 μm and having a mass median particle size between any of the range combinations above. In addition, or in another embodiment of the invention, said particles are essentially spherical. In yet another or additional embodiment of the invention the superabsorbent polymer material has a relatively narrow range of particle sizes, e.g. with the majority (e.g. at least 80% or preferably at least 90% or even at least 95% by weight) of particles having a particle size between 50 μm and 1000 μm, preferably between 100 μm and 800 μm, and more preferably between 200 μm and 600 μm.

The surface of the SAP may be coated, for example, with a cationic polymer. Preferred cationic polymers can include polyamine or polyimine materials. In some embodiments, the SAP may be coated with chitosan materials such as those disclosed in U.S. Pat. No. 7,537,832 B2. In some other embodiments, the SAP may comprise mixed-bed Ion-Exchange absorbent polymers such as those disclosed in WO 99/34841 and WO 99/34842.

The absorbent core will typically comprise only one type of SAP, but it is not excluded that a blend of SAPs may be used. The fluid permeability of a superabsorbent polymer can be quantified using its Urine Permeability Measurement (UPM) value, as measured in the test disclosed European patent application number EP12174117.7. The UPM of the SAP may for example be of at least $10 \times 10^{-7}$ cm$^3$·sec/g, or at least $30 \times 10^{-7}$ cm$^3$·sec/g, or at least $50 \times 10^{-7}$ cm$^3$·sec/g, or more, e.g. at least 80 or $100 \times 10^{-7}$ cm$^3$·sec/g. The flow characteristics can also be adjusted by varying the quantity and distribution of the SAP used in the second absorbent layer.

For most absorbent articles, the liquid discharge occurs predominately in the front half of the article, in particular for diaper. The front half of the article (as defined by the region between the front edge and a transversal line placed at a distance of half L from the front or back edge may therefore comprise most of the absorbent capacity of the core. Thus, at least 60% of the SAP, or at least 65%, 70%, 75% or 80% of the SAP may be present in the front half of the absorbent article, the remaining SAP being disposed in the back half of the absorbent article.

The total amount of SAP present in the absorbent core may also vary according to expected usage. Diapers for newborns may require less SAP than infant or adult incontinence diapers. The amount of SAP in the core may be for example comprised from about 2 to 60 g, in particular from 5 to 50 g or 10 to 40 g. The average SAP basis weight within the (or "at least one", if several are present) deposition area of the SAP may be for example of at least 50, 100, 200, 300, 400, 500 or more g/m². The areas of the channels present in the absorbent material deposition area, if any, are deduced from the absorbent material deposition area to calculate this average basis weight.

Core Wrap 66

The optional core wrap may be made of a single substrate folded around the absorbent material, or may advantageously comprise two (or more) substrates which are attached to another. Typical attachments are the so-called C-wrap and/or sandwich wrap. In a C-wrap, as exemplarily shown in FIG. 2, the longitudinal and/or transversal edges of one of the substrate are folded over the other substrate to form flaps. These flaps are then bonded to the external surface of the other substrate, typically by gluing.

If the core wrap comprises a first substrate 66a and a second substrate 66b these may be made of the same type of material, or may be made of different materials or one of the substrate may be treated differently than the other to provide it with different properties. As the polymers used for nonwoven production are inherently hydrophobic, they are preferably coated with hydrophilic coatings if placed on the fluid receiving side of the absorbent core. It is advantageous that the top side of the core wrap, i.e. the side placed closer to the wearer in the absorbent article, be more hydrophilic than the bottom side of the core wrap. A possible way to produce nonwovens with durably hydrophilic coatings is via applying a hydrophilic monomer and a radical polymerization initiator onto the nonwoven, and conducting a polymerization activated via UV light resulting in monomer chemically bound to the surface of the nonwoven. An alternative possible way to produce nonwovens with durably hydrophilic coatings is to coat the nonwoven with hydrophilic nanoparticles, e.g. as described in WO 02/064877.

Barrier Leg Cuffs 30

The absorbent article comprises a pair of barrier leg cuffs 30. The barrier leg cuffs can be formed from a piece of material, typically a nonwoven, which is partially bonded to the rest of the article so that a portion of the material, the barrier leg cuffs, can be partially raised away and stand up from the plane defined by the topsheet when the article is pulled flat as shown e.g. in FIG. 1. The barrier leg cuffs can provide improved containment of liquids and other bodily exudates approximately at the junction of the torso and legs of the wearer. The barrier leg cuffs extend at least partially between the front edge and the back edge of the diaper on opposite sides of the longitudinal axis and are at least present at the level of the crotch point (P). The barrier leg cuffs are delimited by a proximal edge 32 joined to the rest of the article, typically the topsheet and/or the backsheet, and a free terminal edge 66, which is intended to contact and form a seal with the wearer's skin. The barrier leg cuffs are joined at the proximal edge 32 with the chassis of the article by a bond 33 which may be made for example by gluing, fusion bonding or combination of known bonding means. The bond 33 at the proximal edge 32 may be continuous or intermittent. The side of the bond 33 closest to the raised section of the leg cuffs delimits the proximal edge 32 of the standing up section of the leg cuffs. The distance between the inner sides of these bond 33 define the dry and wet width of the article at this level for the purpose of RCWR test (see below).

The barrier leg cuffs can be integral with the topsheet or the backsheet, or more typically be formed from a separate material joined to the rest of the article. Typically the material of the barrier leg cuffs may extend through the whole length of the diapers but is "tack bonded" to the topsheet towards the front edge and back edge of the article so that in these sections the barrier leg cuff material remains flush with the topsheet. Each barrier leg cuff 30 may comprise one, two or more elastic 36 close to this free distal edge 34 to provide a better seal.

In addition to the barrier leg cuffs 30, the article may comprise gasketing cuffs 26, which are joined to the chassis of absorbent article, in particular the topsheet and/or the backsheet and are placed transversely outwardly relative to the barrier leg cuffs. The gasketing cuffs can provide a better seal around the thighs of the wearer. Usually each gasketing leg cuff will comprise one or more elastic string or elastic element comprised in the chassis of the diaper for example between the topsheet and backsheet in the area of the leg openings.

U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. describe disposable diapers having "stand-up" elasticized flaps (barrier leg cuffs) which improve the containment of the leg regions. U.S. Pat. Nos. 4,695,278 and 4,795,454 issued to Lawson and to Dragoo respectively, describe disposable diapers having dual cuffs, including gasketing cuffs and barrier leg cuffs. All or a portion of the barrier leg and/or gasketing cuffs may be treated with a lotion.

Acquisition-Distribution System 50

The absorbent articles of the invention may comprise an acquisition-distribution layer or system 50 (herein "ADS"). The function of the ADS is to quickly acquire the fluid and distribute it to the absorbent core in an efficient manner. The ADS may comprise one, two or more layers, which may form a unitary layer or remain discrete layers which may be attached to each other. In the examples below, the ADS comprises two layers: a distribution layer 54 and an acquisition layer 52 disposed between the absorbent core and the topsheet, but the invention is not restricted to this example.

Typically, the ADS will not comprise SAP as this may slow the acquisition and distribution of the fluid. The prior art discloses many type of acquisition-distribution system, see for example WO2000/59430 (Daley), WO95/10996 (Richards), U.S. Pat. No. 5,700,254 (McDowall), WO02/067809 (Graef). The ADS may comprise, although not necessarily, two layers: a distribution layer and an acquisition layer, which will now be exemplified in more details.

Distribution Layer 54

The distribution layer may for example comprise at least 50% by weight of cross-linked cellulose fibers. The cross-linked cellulosic fibers may be crimped, twisted, or curled, or a combination thereof including crimped, twisted, and curled. This type of material has been used in the past in disposable diapers as part of an acquisition system, for example US 2008/0312622 A1 (Hundorf. The cross-linked cellulosic fibers provide higher resilience and therefore higher resistance to the first absorbent layer against the compression in the product packaging or in use conditions, e.g. under baby weight. This provides the core with a higher void volume, permeability and liquid absorption, and hence reduced leakage and improved dryness.

The distribution layer comprising cross-linked cellulose fibers of the invention may comprise other fibers, but this layer may advantageously comprise at least 50%, or 60%, or 70%, or 80%, or 90% or even up to 100%, by weight of the layer, of cross-linked cellulose fibers (including the cross-linking agents). Examples of such mixed layer of cross-linked cellulose fibers may comprise about 70% by weight of chemically cross-linked cellulose fibers, about 10% by weight polyester (PET) fibers, and about 20% by weight untreated pulp fibers. In another example, the layer of cross-linked cellulose fibers may comprise about 70% by weight chemically cross-linked cellulose fibers, about 20% by weight lyocell fibers, and about 10% by weight PET fibers. In another example, the layer may comprise about 68% by weight chemically cross-linked cellulose fibers, about 16% by weight untreated pulp fibers, and about 16% by weight PET fibers. In another example, the layer of cross-linked cellulose fibers may comprise from about 90-100% by weight chemically cross-linked cellulose fibers.

The distribution layer 54 may be a material having a water retention value of from 25 to 60, preferably from 30 to 45, measured as indicated in the procedure disclosed in U.S. Pat. No. 5,137,537.

The distribution layer may typically have an average basis weight of from 30 to 400 g/m$^2$, in particular from 100 to 300 g/m$^2$. The density of the distribution layer may vary depending on the compression of the article, but may be of between 0.03 to 0.15 g/cm$^3$, in particular 0.08 to 0.10 g/cm$^3$ measured at 0.30 psi (2.07 kPa).

Acquisition Layer 52

The ADS may comprise an acquisition layer 52. The acquisition layer may be disposed between the distribution layer 54 and topsheet 22. The acquisition layer 52 may typically be or comprise a non-woven material, for example a SMS or SMMS material, comprising a spunbonded, a melt-blown and a further spunbonded layer or alternatively a carded chemical-bonded nonwoven. The non-woven material may in particular be latex bonded. Exemplary upper acquisition layers 52 are disclosed in U.S. Pat. No. 7,786,341. Carded, resin-bonded nonwovens may be used, in particular where the fibers used are solid round or round hollow PET staple fibers (50/50 or 40/60 mix of 6 denier and 9 denier fibers). An exemplary binder is a butadiene/styrene latex. Non-wovens have the advantage that they can be manufactured outside the converting line and stored and used as a roll of material.

Further useful non-wovens are described in U.S. Pat. No. 6,645,569 to Cramer et al., U.S. Pat. No. 6,863,933 to Cramer et al., U.S. Pat. No. 7,112,621 to Rohrbaugh et al., and co patent applications US 2003/148684 to Cramer et al. and US 2005/008839 to Cramer et al.

The acquisition layer 52 may be stabilized by a latex binder, for example a styrene-butadiene latex binder (SB latex). Processes for obtaining such lattices are known, for example, from EP 149 880 (Kwok) and US 2003/0105190 (Diehl et al.). In certain embodiments, the binder may be present in the acquisition layer 52 in excess of about 12%, about 14% or about 16% by weight. SB latex is available under the trade name GENFLO™ 3160 (OMNOVA Solutions Inc.; Akron, Ohio).

A further acquisition layer may be used in addition to a first acquisition layer described above. For example a tissue layer may be placed between the first acquisition layer and the distribution layer. The tissue may have enhanced capillarity distribution properties compared to the acquisition layer described above. The tissue and the first acquisition layer may be of the same size or may be of different size, for example the tissue layer may extend further in the back of the absorbent article than the first acquisition layer. An example of hydrophilic tissue is a 13-15 gsm high wet strength made of cellulose fibers from supplier Havix.

Fastening System

The absorbent article may include a fastening system. The fastening system can be used to provide lateral tensions about the circumference of the absorbent article to hold the absorbent article on the wearer as is typical for taped diapers. This fastening system is not necessary for training pant article since the waist region of these articles is already bonded. The fastening system usually comprises a fastener such as tape tabs (also referred to as adhesive tabs), hook and loop fastening components, interlocking fasteners such as tabs & slots, buckles, buttons, snaps, and/or hermaphroditic fastening components, although any other known fastening means are generally acceptable. A landing zone is normally provided on the front waist region for the fastener to be releasably attached. Some exemplary surface fastening systems are disclosed in U.S. Pat. Nos. 3,848,594, 4,662,875, 4,846,815, 4,894,060, 4,946,527, 5,151,092 and 5,221,274 issued to Buell. An exemplary interlocking fastening system is disclosed in U.S. Pat. No. 6,432,098. The fastening system may also provide a means for holding the article in a disposal configuration as disclosed in U.S. Pat. No. 4,963,140 issued to Robertson et al.

The fastening system may also include primary and secondary fastening systems, as disclosed in U.S. Pat. No. 4,699,622 to reduce shifting of overlapped portions or to improve fit as disclosed in U.S. Pat. Nos. 5,242,436, 5,499,978, 5,507,736, and 5,591,152.

Back Ears 40 and Front Ears 46

The absorbent article may comprise front ears 46 and back ears 40 as is known in the art. The ears can be integral part of the chassis, for example formed from the topsheet and/or backsheet as side panel. Alternatively, as represented on FIG. 1, they may be separate elements attached by gluing and/or heat embossing or pressure bonding. The back ears 40 are advantageously stretchable to facilitate the attachment of the adhesive tabs 42 on the landing zone 44 and maintain the taped diapers in place around the wearer's waist. The back ears 40 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

Elastic Waist Feature

The absorbent article may also comprise at least one elastic waist feature (not represented) that helps to provide improved fit and containment. The elastic waist feature is generally intended to elastically expand and contract to dynamically fit the wearer's waist. The elastic waist feature preferably extends at least longitudinally outwardly from at least one waist edge of the absorbent core 20 and generally forms at least a portion of the end edge of the absorbent article. Disposable diapers can be constructed so as to have two elastic waist features, one positioned in the front waist region and one positioned in the back waist region. The elastic waist feature may be constructed in a number of different configurations including those described in U.S. Pat. Nos. 4,515,595, 4,710,189, 5,151,092 and 5,221,274.

Relations Between the Layers

Typically, adjacent layers and components will be joined together using conventional bonding method such as adhesive coating via slot coating or spraying on the whole or part of the surface of the layer, or thermo-bonding, or pressure bonding or combinations thereof. This bonding is not represented in the Figures (except for the bonding by bonds 33 between the raised elements of the barrier leg cuffs 30 with the topsheet 22) for clarity and readability but bonding between the layers of the article should be considered to be present unless specifically excluded. Adhesives may be typically used to improve the adhesion of the different layers, for example between the backsheet and the core wrap. The glue may be any standard hotmelt glue as known in the art.

If an acquisition layer 52 is present, it may be advantageous that this acquisition layer is larger than or least as large as the distribution layer 54 in the longitudinal and/or transversal dimension. In this way the distribution layer 54 can be deposited on the acquisition layer 52 during the manufacturing process before assembling these layers in the finished article. This simplifies handling, in particular if the acquisition layer is a nonwoven which can be unrolled from a roll of stock material. The distribution layer may also be deposited directly on the absorbent core's upper side of the core wrap or another layer of the article. Also, an acquisition layer 52 larger than the distribution layer allows to directly glue the acquisition layer to the storage core (at the larger areas). This can give increased integrity to the article and better liquid communication.

The absorbent core and in particular its absorbent material deposition area may advantageously be at least as large and long and advantageously at least partially larger and/or longer than the acquisition-distribution system (ADS). This is because the absorbent material in the core can usually more effectively retain fluid and provide dryness benefits across a larger area than the ADS. The absorbent article may have a rectangular SAP layer and a non-rectangular (shaped) ADS. The absorbent article may also have a rectangular (non-shaped) ADS and a rectangular layer of SAP.

Method of Making the Article

The absorbent articles of the invention may be made by any conventional methods known in the art. In particular the articles may be hand-made or industrially produced at high speed.

Experimental Settings

The values indicated herein are measured according to the methods indicated herein below, unless specified otherwise. All measurements are performed at 21±2° C. and 50±20% RH, unless specified otherwise. All samples should be kept at least 24 hours in these conditions to equilibrate before conducting the tests, unless indicated otherwise. All measurements should be reproduced on at least 4 samples and the average value obtained indicated, unless otherwise indicated.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for personal hygiene, designed to absorb and contain bodily exudates selected from the group of a diaper, a training pant and an incontinence insert, the absorbent article having a front edge and a rear edge, a longitudinal axis extending in a longitudinal direction of the article, the article having a length L as measured along the longitudinal axis from the front edge to the back edge, the absorbent article comprising: an indication means for indicating both the presence of such bodily exudates and for indicating body temperature or fever, the indication means consisting of a color-changing pH-sensitive chemical and a color-changing thermochromic material selected from the group consisting of thermochromic inks, thermochromic dyes, thermochromic liquid crystalline materials, and mixtures thereof, and wherein the indication means is in a sheet form, wherein the absorbent article and the indication means form one integral unit, the article further comprising an indication device, which comprises a housing and a connection means, such that the indication device is configured to be attached to the absorbent article and be detached from the absorbent article, wherein the indication device comprises a color sensor and a light emitting device configured to direct light onto an area of the absorbent article comprising the color-changing indication means, and wherein the color sensor is a hyperspectral sensor which is sensitive to visible light and to light in the near IR range and is optimized for assessing the color of the color-changing indication means.

2. An absorbent article according to claim 1, wherein the absorbent article comprises a topsheet facing the wearer, a backsheet, generally co-extensive with the topsheet and facing away from the wearer and an absorbent core, encased between the topsheet and the backsheet and wherein the indication means is provided between the backsheet and the core.

* * * * *